United States Patent
Schultheiss

(10) Patent No.: US 9,415,408 B2
(45) Date of Patent: Aug. 16, 2016

(54) DRIVE DEVICE OF A METERING AND MIXING DEVICE

(71) Applicant: SIKA TECHNOLOGY AG, Baar (CH)

(72) Inventor: Christian Schultheiss, Pfäffikon (CH)

(73) Assignee: SIKA TECHNOLOGY AG, Baar (CH)

( * ) Notice: Subject to any disclaimer, the term of this patent is extended or adjusted under 35 U.S.C. 154(b) by 109 days.

(21) Appl. No.: 14/311,923

(22) Filed: Jun. 23, 2014

(65) Prior Publication Data

US 2014/0346251 A1 Nov. 27, 2014

Related U.S. Application Data

(63) Continuation of application No. PCT/EP2012/076508, filed on Dec. 20, 2012.

(30) Foreign Application Priority Data

Dec. 21, 2011 (EP) .................................... 11194940

(51) Int. Cl.
*B67D 7/70* (2010.01)
*B05B 7/24* (2006.01)
(Continued)

(52) U.S. Cl.
CPC . *B05B 7/24* (2013.01); *A61C 5/064* (2013.01); *B01F 13/0023* (2013.01);
(Continued)

(58) Field of Classification Search
CPC ...................... B05C 17/0133; B05C 17/00553; B05C 17/00566; B05C 17/00576; B05C 17/00596; B05C 17/0103; B05C 17/014; B05C 17/0116; A61C 5/064; B01F 13/0023; B01F 15/0237; B01F 15/042; B01F 2215/0027; B01F 2215/0039; B01F 13/0027; B05B 7/24
See application file for complete search history.

(56) References Cited

U.S. PATENT DOCUMENTS 3,302,832 A * 2/1967 Anderson ............. B01F 13/002
222/100
4,934,827 A * 6/1990 Taschke ............ B05C 17/00553
222/137
(Continued)

FOREIGN PATENT DOCUMENTS

DE 32 33 366 A1 9/1983
EP 0 057 465 A2 8/1982
(Continued)

OTHER PUBLICATIONS

International Search Report (PCT/ISA/210) mailed on Feb. 5, 2013, by the European Patent Office as the International Searching Authority for Int'l Appln No. PCT/EP2012/076508. (with English translation).
(Continued)

*Primary Examiner* — Patrick M Buechner
(74) *Attorney, Agent, or Firm* — Buchanan Ingersoll & Rooney PC

(57) ABSTRACT

A drive apparatus of a metering and mixing device is provided for multi-component materials, for example, for multi-component adhesives. The metering and mixing device can have at least two cartridge-accommodating devices for accommodating replaceable cartridges having individual material components, and a discharging device for simultaneously discharging the material components from the cartridges through the component outlets by discharging plungers that plunge into the cartridge-accommodating device and a mixing device. A transmission unit connects a drive machine, and has a coupling for forced connection of a discharge of at least two material components by correspondingly synchronized actuation of discharging plungers by respective discharging rods.

19 Claims, 6 Drawing Sheets

(51) Int. Cl.
*B05C 17/005* (2006.01)
*A61C 5/06* (2006.01)
*B01F 13/00* (2006.01)
*B01F 15/02* (2006.01)
*B01F 15/04* (2006.01)
*B05C 17/01* (2006.01)

(52) U.S. Cl.
CPC .......... *B01F 15/0237* (2013.01); *B01F 15/042* (2013.01); *B05C 17/00553* (2013.01); *B05C 17/00566* (2013.01); *B05C 17/00576* (2013.01); *B05C 17/00596* (2013.01); *B05C 17/0103* (2013.01); *B05C 17/014* (2013.01); *B01F 2215/0027* (2013.01); *B01F 2215/0039* (2013.01); *B05C 17/0116* (2013.01); *B05C 17/0133* (2013.01)

(56) References Cited

U.S. PATENT DOCUMENTS

| | | | | |
|---|---|---|---|---|
| 4,986,443 | A * | 1/1991 | Saur | B05C 17/00553 222/1 |
| 5,104,005 | A * | 4/1992 | Schneider, Jr. | B05C 17/00553 222/137 |
| 5,203,476 | A * | 4/1993 | Keller | B05C 17/0103 222/136 |
| 5,207,357 | A * | 5/1993 | Aronie | B05C 17/00553 222/134 |
| 5,860,739 | A * | 1/1999 | Cannon | A61C 5/062 222/137 |
| 2003/0022128 | A1 | 1/2003 | Heymann et al. | |
| 2008/0144426 | A1 | 6/2008 | Janssen et al. | |
| 2009/0039113 | A1 | 2/2009 | Hsu et al. | |
| 2010/0091607 | A1* | 4/2010 | Meyer | A61C 5/064 366/151.2 |
| 2012/0148980 | A1 | 6/2012 | Gramann | |
| 2013/0277390 | A1 | 10/2013 | Buck et al. | |
| 2014/0092704 | A1 | 4/2014 | Janssen et al. | |
| 2014/0301156 | A1* | 10/2014 | Rahm | B05C 17/00566 366/184 |

FOREIGN PATENT DOCUMENTS

| | | |
|---|---|---|
| EP | 1 279 379 A1 | 1/2003 |
| EP | 2 468 415 A1 | 6/2012 |
| WO | WO 2008/076941 A1 | 6/2008 |
| WO | WO 2011/025831 A1 | 3/2011 |

OTHER PUBLICATIONS

Written Opinion (PCT/ISA/237) mailed on Feb. 5, 2013, by the European Patent Office as the International Searching Authority for International Application No. PCT/EP2012/076508. (with English translation).

International Search Report (PCT/ISA/210) mailed on Jan. 24, 2013, by the European Patent Office as the International Searching Authority for International Application No. PCT/EP2012/075155. (with English translation).

Written Opinion (PCT/ISA/237) mailed on Jan. 24, 2013, by the European Patent Office as the International Searching Authority for International Application No. PCT/EP2012/075155. (with English translation).

International Search Report (PCT/ISA/210) mailed on Jan. 18, 2013, by the European Patent Office as the International Searching Authority for International Application No. PCT/EP2012/075192. (with English translation).

Written Opinion (PCT/ISA/237) mailed on Jan. 18, 2013, by the European Patent Office as the International Searching Authority for International Application No. PCT/EP2012/075192. (with English translation).

* cited by examiner

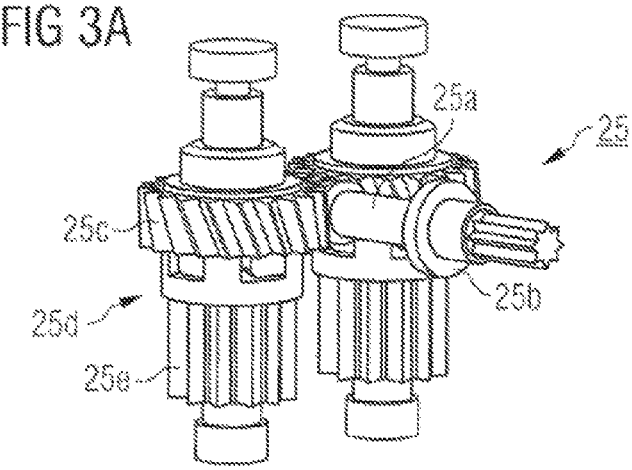
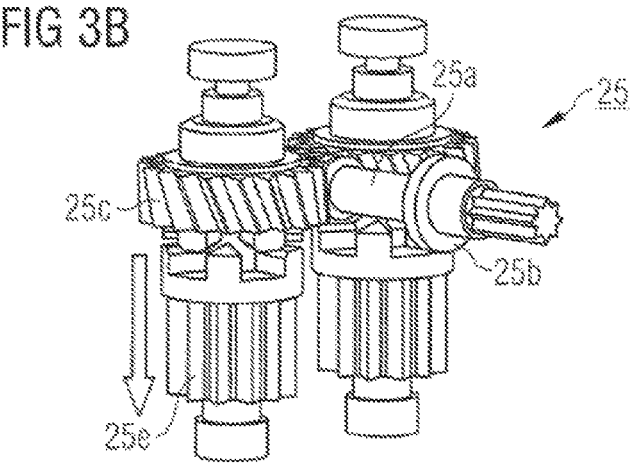
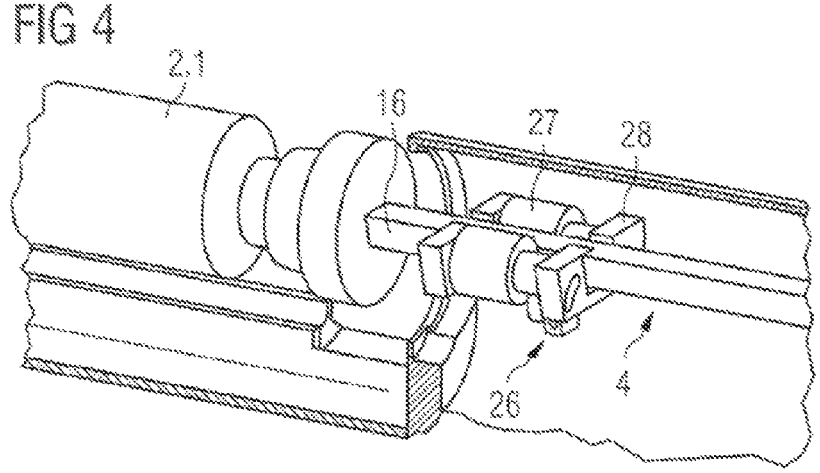

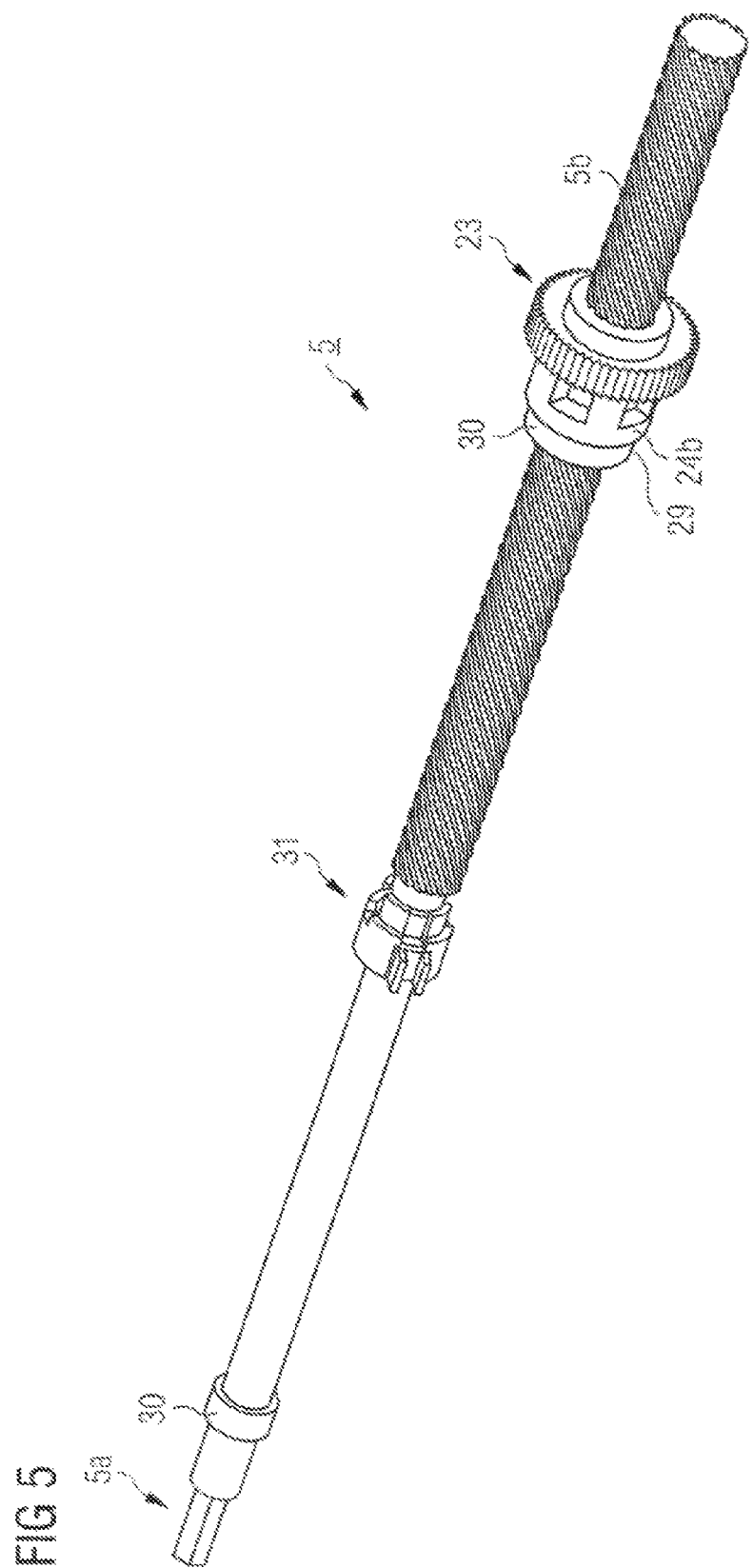

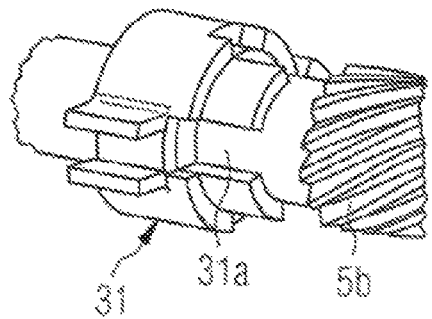
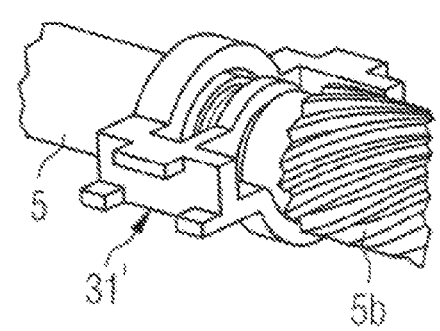
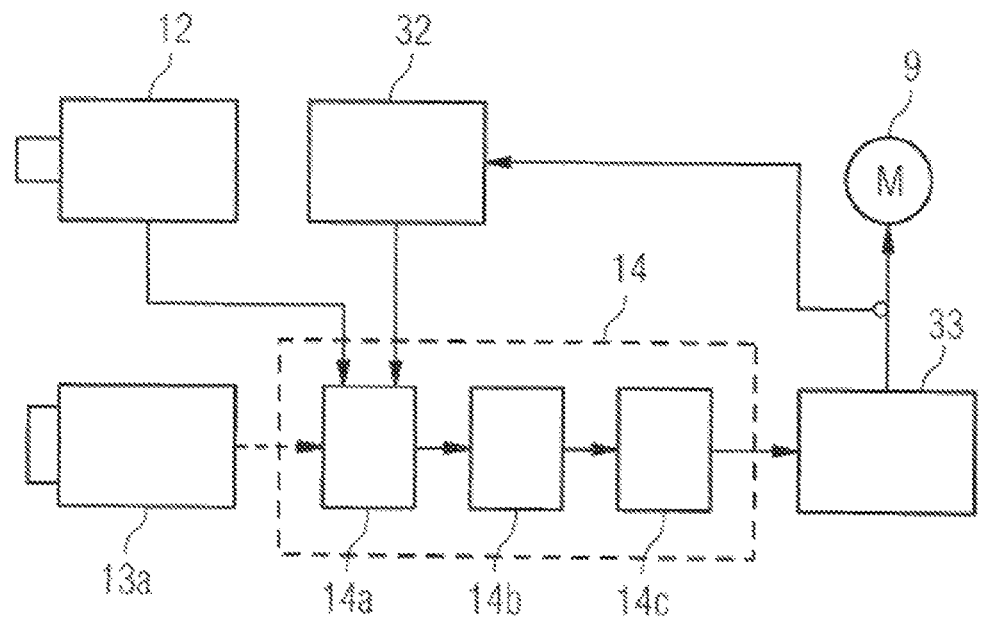

DRIVE DEVICE OF A METERING AND MIXING DEVICE

RELATED APPLICATION(S)

This application claims priority as a continuation application under 35 U.S.C. §120 to PCT/EP2012/076508, which was filed as an International Application on Dec. 20, 2012 designating the U.S., and which claims priority to European Application 11194940.0 filed in Europe on Dec. 21, 2011. The entire contents of these applications are hereby incorporated by reference in their entireties.

FIELD

The disclosure relates to a drive apparatus of a metering and mixing device for multi-component materials, for example, multi-component adhesives, which can have at least two interconnected cartridge-accommodating devices for accommodating replaceable cartridges having individual material components, a discharge device for simultaneously discharging the material components from the cartridges through component outlets by discharging plungers that plunge into the cartridge-accommodating device, wherein at least one discharging plunger can have a threading for plunger rotation to create a forward drive of this discharge plunger, and which can have a mixing device which is connected to the component outlets and mix the discharged material components and dispense them in a mixed state.

BACKGROUND INFORMATION

A metering and mixing device is disclosed in European Patent Application 10 196 972.3 of the applicant.

A metering and mixing device for mixing a dental impression compound is disclosed in DE 3 233 366 A1. This device can include a stirring unit, designed as a disposable part, with a base body that has a mixing chamber, several feed channels opening separately into the mixing chamber for the components of the impression compound, and outlet openings for the mixed impression compound. The stirring unit also has a stirrer arranged rotatably in the mixing chamber, which is driven by a drive apparatus against which the stirring unit is held removably. The components of an impression compound can be held in reservoir cylinders and can be forced by plungers into the mixing chamber, and after mixing, can be forced out through the outlet opening into the impression tray. The speed of advance of the actuating drives of the plungers can be varied so that both a ratio of the plunger advance speed, which determines the setting time of the impression compound and the overall advance or the duration of advance and thus the quantity of impression compound, can be controlled.

Reference is also made to EP 0 057 465 A2, WO 2011/025831 A1, US 2009/039112 A1, WO 2008/076941 A1 and EP 2 279 379 A1.

SUMMARY

A drive apparatus of a metering and mixing device for multi-component materials is disclosed, the drive apparatus comprising: at least two cartridge-accommodating devices configured to accommodate replaceable cartridges with individual material components; a discharging device configured to simultaneous discharge the material components from the cartridges through component outlets with the aid of discharging plungers for plunging into the cartridge-accommodating device or cartridges; a mixing device connected to the component outlets for mixing discharged material components and discharging them in mixed form; and a transmission unit for connection of a drive machine, wherein the transmission unit includes a coupling for a forced connection of the discharge of at least two material components by correspondingly synchronized actuation of corresponding discharging plungers via one discharging rod each.

A device for multi-component materials is disclosed, the device comprising: an integrated electric drive machine; an operating and control unit; a battery power supply for the integrated electric drive machine and the operating and control unit; and a drive apparatus of a metering and mixing device, the drive apparatus including: at least two cartridge-accommodating devices configured to accommodate replaceable cartridges with individual material components; a discharging device configured to simultaneous discharge the material components from the cartridges through component outlets with the aid of discharging plungers for plunging into the cartridge-accommodating device or cartridges; a mixing device connected to the component outlets for mixing the discharged material components and discharging them in mixed form; and a transmission unit for connection of a drive machine, wherein the transmission unit includes a coupling for a forced connection of the discharge of at least two material components by correspondingly synchronized actuation of the corresponding discharging plungers via one discharging rod each.

BRIEF DESCRIPTION OF THE DRAWINGS

The disclosure will now be further explained by way of exemplary embodiments and with reference to the accompanying drawings, in which:

FIGS. 3A and 3B are perspective views of an exemplary embodiment of transmission component serving to drive the gear rack;

FIG. 4 is a schematic diagram of an exemplary drive of the gear rack;

FIG. 5 is a perspective view of an exemplary embodiment of the second discharging rod of the application device according to FIG. 1;

FIGS. 7A and 7B are schematic diagrams in the form of perspective views of an exemplary second discharging rod according to FIG. 5;

FIG. 8 is a block diagram of an exemplary embodiment of a sensor that forms part of the drive device 1B of the application apparatus according to FIG. 1.

DETAILED DESCRIPTION

Figure 1:
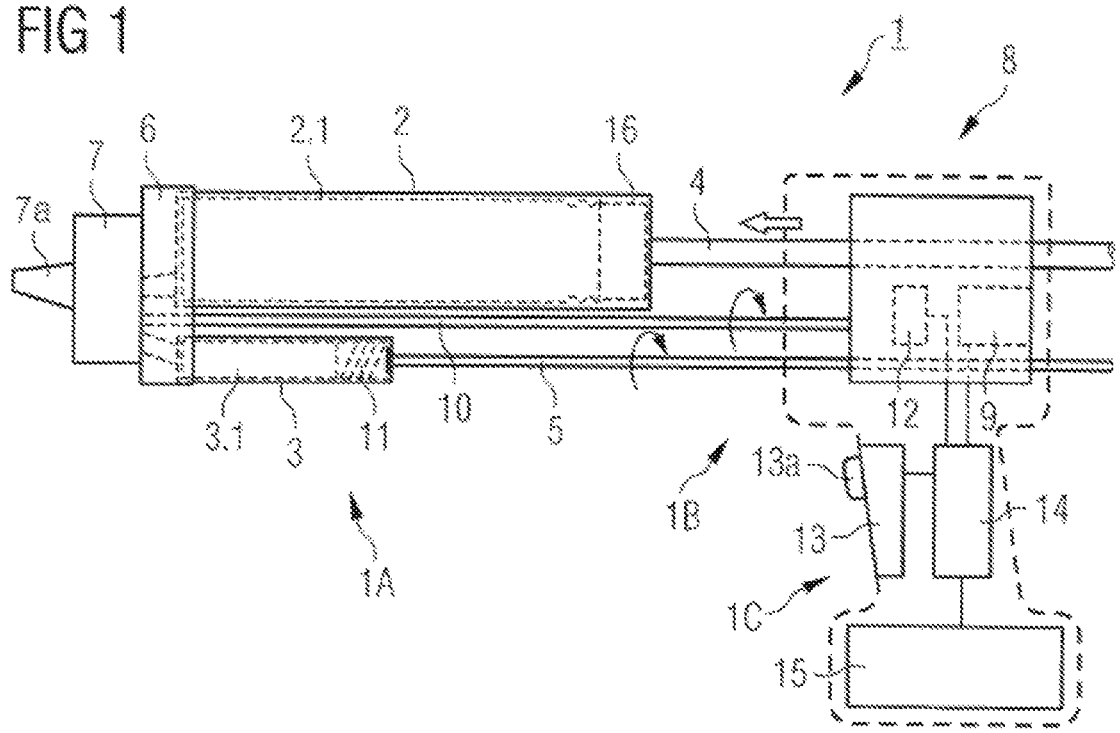
FIG. 1 is side view of an exemplary application device according to the disclosure for a 2-component adhesive.

A drive apparatus of a metering and mixing device for multi-component materials is disclosed, for example, multi-component adhesives, which can have at least two interconnected cartridge-accommodating devices for accommodating replaceable cartridges having individual material components, a discharge device for simultaneously discharging the material components from the cartridges through component outlets by means of discharging plungers that plunge into the cartridge-accommodating device, wherein at least one discharging plunger can have a threading for plunger rotation to create a forward drive of the discharge plunger, and can have a mixing device which is connected to the component outlets for mixing discharged material components and dispensing them in the mixed state.

The disclosure can include the driving of a metering and mixing device for multi-component materials, for example, so that a certain component is only discharged if another component that is supposed to react with the first is supplied simultaneously, and wherein the discharge can occur, even if the components, for example, are contained in cartridges of different design and different sizes and/or have different mechanical properties. In accordance with an exemplary embodiment, a transmission unit for connecting a drive machine can be provided, wherein the transmission unit can have a coupling means for forced connection of the discharge of at least two material components by correspondingly synchronized actuation of the corresponding discharging plungers by means of respective discharging rods.

For example, the transmission unit can be designed (i.e., configured) for axial drive of a first discharging plunger for discharging a material component A driven over a first discharging rod and for rotary drive of a second discharging plunger provided with threading and driven over a second spindle-like discharging rod for discharging a material component B, and it can have a transmission unit axially movable under reaction pressure during discharging of material component A. In accordance with an exemplary embodiment, a switchable coupling device can connect the second discharging rod with the drive machine when the movable unit has advanced by a certain amount under the reaction pressure. The coupling device can be automatically switchable, for example, upon reaching a certain reaction pressure value during the discharge of material component A.

In accordance with an exemplary embodiment, the automatic switching function of the movable component group (or the coupling element associated to it) can be performed with a counter-pressure spring element, which can supply a counterforce directed against the reaction pressure during discharge of component A to establish the action point of the coupling unit. In an exemplary embodiment, the component group of the coupling element can have a pressure spring element connected to it to supply an adjusting pressure force directed in parallel to the counter-pressure during discharge of component A for fine adjustment of the action point of the coupling device.

In an exemplary embodiment, the switchable coupling device can have a first coupling element, which can be positioned in the axial direction, essentially immovably with reference to the drive machine or apparatus housing. The execution and positioning of a second coupling element can be established such that at a fixed pressure value, under the pressure emerging from the cartridge of material component A and transferred over the first drive plunger and the first discharging rod, it advances with the movable transmission component group. This coupling element can engage with the first coupling element in moving the component group mentioned.

In an exemplary embodiment, the switchable coupling device can be a form-locking coupling, for example, a claw coupling. In accordance with an exemplary embodiment, the coupling elements of the form-locking coupling can be self-locating elements. In an exemplary embodiment, the switchable coupling can be a force-locking coupling, for example, a frictional coupling.

In an exemplary embodiment, the discharging rod associated to the discharge plunger for component A can be a known gear rack, and the corresponding parts of the transmission unit can be adapted. For example, at least one drive gear, for example, two drive gears, in the transmission can be provided for meshing with the gear rack, which can, for example, be designed as one or more coil gears. In accordance with an exemplary embodiment, the first drive rod can be a spindle, and can have associated to it, for example, a ball spindle drive with a removable threaded sleeve or a ball spindle drive with threaded surrounding spindle.

In an exemplary embodiment, the drive gears of the transmission unit engaged with the first discharging rod during normal operation of the transmission unit can be movable relative to the discharging rods to decouple them from the discharging rods and as a result, can provide a relatively resistance-free manual withdrawal for reloading the mixing and metering device.

In an exemplary embodiment, the drive of the second discharge plunger for discharging material component B can be achieved with novel means. For example, the corresponding discharging rod in the rear part of its lengthwise dimension, based on the position of use, can have a spiral-toothed, non-self-locking spindle section and at the front end an engaging element engaging in the second discharge plunger, and the corresponding section of the transmission unit can include a drive gear with interior spiral teeth adapted to the spiral teeth of the spindle section.

In an exemplary embodiment, the transmission unit can include a rotary shaft connection section for connecting a drive shaft of an active mixer provided in the metering and mixing device.

FIG. 1 shows a side view (schematic representation) of an exemplary application device 1 according to the disclosure, which can include a metering and mixing device 1A, a corresponding drive device 1B, and an apparatus body 1C.

The metering and mixing device 1A can include, for example, two cartridge-accommodating devices 2 and 3 with different diameters and different lengths for a tubular sack 2.1 and a solid cartridge 3.1. The larger cartridge-accommodating device 2 can be actuated with an axially movable first drive plunger ("linear plunger") 16 that is connected to a first drive rod (gear rack) 4 and can be advanced by this in a linear fashion into the cartridge-accommodating device 2. The cartridge-accommodating device 3, which can have a substantially smaller diameter and can also be substantially shorter than the cartridge-accommodating device 2, according to the disclosure can be actuated by a second drive plunger ("rotary plunger"), which on its outside can have a threading that can engage with the inner wall of the cartridge-accommodating device 3 or a cartridge 3.1 inserted therein and can generate forward drive by rotation.

The drive unit 1B can include a transmission unit 8, which can have a single drive input side and three different drive outlet sides. In accordance with an exemplary embodiment, these can be an outlet for the linearly advanced gear rack 4, or an outlet for a second discharging rod 5, and an outlet for a likewise rotating drive shaft 10, which can operate a rotary mixer 7. The two cartridge-accommodating devices 2 and 3 on the discharge side can be connected with a cartridge coupling 6, through which the material also present in the cartridge-accommodating devices 2 and 3 can be delivered from the component outlets to the rotary mixer 7, which can be connected to the cartridge coupling 6. The design of such rotary mixer is known. For example, the rotary mixer can have a drive tip 7a attached at the front, through which the mixed material is ultimately discharged.

The drive unit 8 in the exemplary embodiment of the metering and mixing device 1 shown in FIG. 1 can be driven with the aid of an electric machine 9. A microswitch 12 can be provided, the function of which will be described further below. The device body 1C can include an operating unit 13 with a manually actuatable on and off switch 13a, a drive control unit 14 and a battery pack 15.

Figure 2:
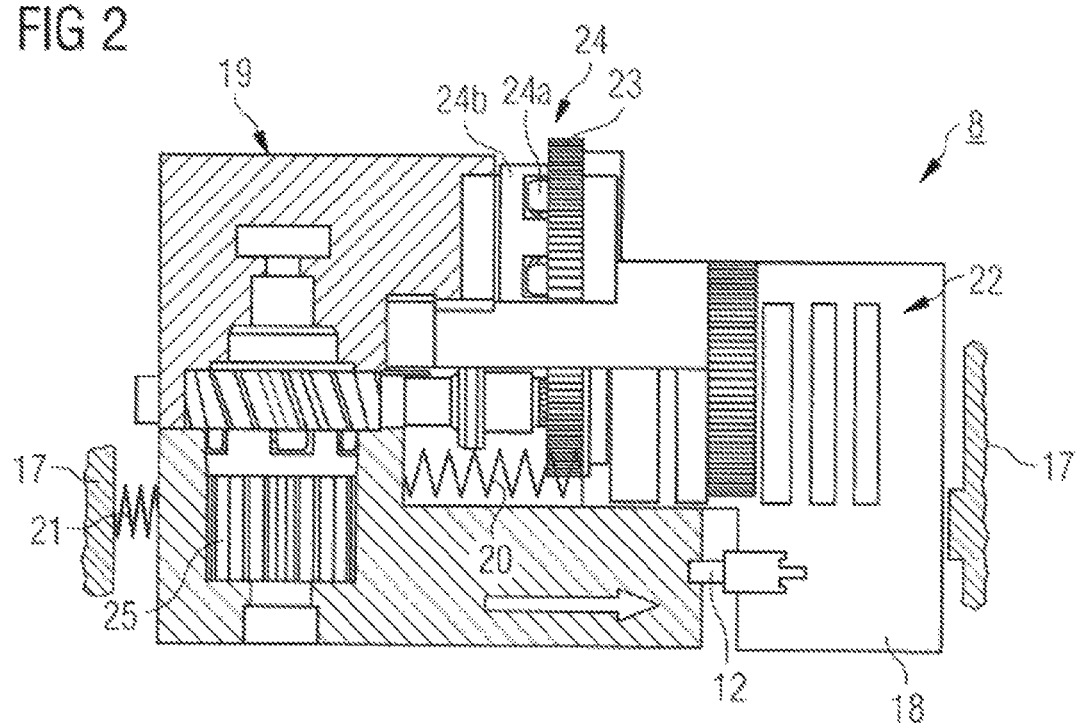
FIG. 2 is a representation of an exemplary structure of a transmission unit of the exemplary application device according to FIG. 1.
Figure 6:
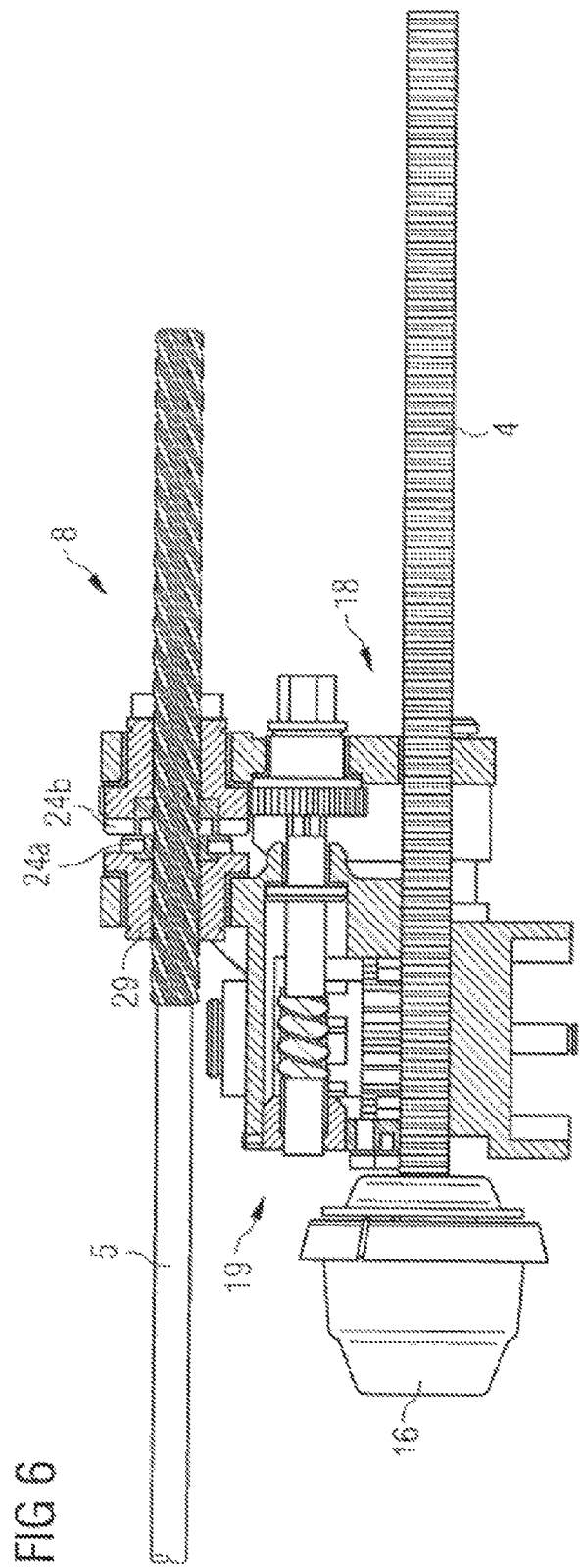
FIG. 6 is a cutaway view of an exemplary embodiment of the transmission unit of the application device according to FIG. 1.

FIGS. 2 and 6 show the structure of an exemplary embodiment of the drive unit 8. The method of presentation of FIG. 2 and additional figures differs from that in FIG. 1 in that in FIG. 2, the transmission components forming part of the gear rack 4 can be at the bottom and the components belonging to the second discharging rod 5 can be located at the top.

The transmission unit 8 can include a first component group 18 fixed in place relative to a wall of an apparatus housing 17 of the application device and a second component group 19 carried movably in the apparatus housing. The two transmission component groups 18 and 19 can be clamped elastically together by means of a counter-pressure spring 20 (shown here symbolically) and the movable component group 19 can be elastically supported against the apparatus housing 17 with an additional spring element 21, which can also be designated as a pressure spring element in the remainder of the document. The first component group 18 can include a planetary transmission 22, which can be in contact with a drive pinion of the drive machine, and the output 23 for driving the spindle-like second drive rod and driven gears for the first discharging rod (gear rack) and the drive shaft of the mixer.

At the output for the second discharging rod, a switchable coupling (claw coupling) 24 is provided, which can include a first coupling element 24a fixed in place relative to the first component group 18 and a second coupling element 24b fixed in place relative to the second component group 19. A transmission component 25 can be placed in the second component group 19 for driving the first discharging rod (gear rack) will be described herein.

The microswitch 12 can be permanently attached to the first component group 18 and can be positioned such that it is actuated in a predetermined movement position of the second component group 19.

The functioning of the two-part design of the transmission unit 8 with the spring supports mentioned and the microswitch is as follows in a simplified exemplary description:

In the switched-off state of the application device, the second component group 19 has advanced forward relative to the first component group 18 of the transmission unit 8 due to the force of the counter-pressure spring 20 that the first and second coupling elements 24a, 24b of the switchable coupling 24 can be not connected and the second component group 19 also does not touch the microswitch 12. The exact resting position of the second component group 19 is adjusted by suitable selection of the back-pressure spring 20 and the forward-pressure spring 21, adapted to one another, and the response behavior of the mounting of the second component group 19 on startup of the apparatus.

On startup the drive force can proceed from the drive machine over the planetary transmission 22 and the transmission component 25 to the gear rack 4 and causes it to move in the drive direction of the metering and mixing device (to the left in FIG. 1 and FIG. 2). As soon as the first discharge plunger 16 encounters the end of the filled cartridge 2.1 facing it, a reactive pressure can build up, because of the viscosity of the material component contained therein and can be transmitted over the gear rack 4 to its drive pinion (see FIG. 3A) and can be transmitted over its mounting to the second component group 19. It can cause movement of the second component group 19 relative to the first component group 18 against the spring force of the counter-pressure spring 20. As soon as a certain shift amount is reached, the coupling elements 24a, 24b can engage, and the flow of force from the drive machine can also reach the spindle-like second discharging rod 5, setting this into rotation and driving the self-cutting plunger. At the same time, the microswitch 12 can be actuated by the movement of the second component group 19. In accordance with an exemplary embodiment, the function connected with this process is described herein.

As a result of this design and the resulting sequence it can be relatively ensured that discharge of the component B contained in cartridge 3.1 takes place, for example, only if the component A of the multi-component system contained in cartridge 2.1 is also discharged. This is also true if a partially emptied cartridge with component A is placed in the device at point 1 and the operation is started in the fully retracted initial position of the gear rack 4. For example, this then moves forward in idle mode, and the second transmission component group 19 remains in the outlet state shifted relative to the first component group 18, until the first discharge plunger 16 encounters the end of the partially filled cartridge. Only at this time is a reaction force built up there, which presses the second component group 19 against the first component group 18 and thus closes the switchable coupling 24, so that the drive force is also introduced into the second discharging rod (spindle) 5. In this application as well, therefore, component B is only discharged at the correct time.

FIGS. 3A and 3B show an exemplary embodiment of the transmission component serving to drive the first discharging rod (gear rack 4), a coupling-capable screw drive 25 in the coupled-in (FIG. 3A) and uncoupled (FIG. 3B) states. The screw drive can include a screw 25a with a spline shaft, which can be supported in an axial bearing 25b and can be driven over a drive gear of the planetary transmission. Two coil gears 25c with helical teeth can be engaged with the screw 25a, with a claw coupling 25d associated to each of them. With the displaceable coupling element of this coupling 25d in each case a straight-toothed drive pinion 25e can be permanently connected, which in the engaged state of the coupling 25d can move along with the coil gear 25c and can transmit the drive force to the gear rack (no. 4 in FIG. 1), not shown here, with which it meshes. In the disengaged state shown in FIG. 3B the pinions 25e can essentially rotate freely, so that the gear rack supported between them and engaging with them can be moved axially practically without resistance, such that it can be easily drawn back to reload the application device with a full cartridge 2.1 (FIG. 1).

FIG. 4 is a schematic diagram in the form of a perspective view of an exemplary drive of the gear rack as shown in FIG. 1. The gear rack 4 can be driven over a spur gear transmission 26 and two screws 27, which can be pivotably supported in a guide bar 28. By pivoting this screw 27 by means of an actuating lever, its engagement with the gear rack 4 can be undone, so that it is once again made possible to withdraw the gear rack almost without resistance. In an exemplary embodiment, the gear rack 4 can be driven over two pinions directly meshing in the flanks thereof, with their rotational axes perpendicular to the length of the gear rack. This drive concept is familiar to those skilled in the art and therefore will not be illustrated or described in greater detail.

FIG. 5 shows a perspective view of an exemplified embodiment of the second discharging rod 5. As shown in FIG. 5, the second discharging rod 5 at its end (on the left in the figure) can have an engaging element 5a, which can be a polygon for engaging in a correspondingly-shaped engagement device on the discharging rod plunger 11 (FIG. 1), which represents a separate part from the discharging rod and for example can be part of the cartridge 3.1 and can be delivered with it. The opposite end section 5b of the discharging rod 5 can have a spiral-toothed system with a high flank lead, resulting in non-self-locking behavior. In this terminal section 5b the spindle-like discharging rod can engage with an inner-toothed drive gear 29 of the transmission unit corresponding to the exterior threading of section 5b, which can be permanently connected to or made in one piece with the second coupling element 24b of the switchable coupling 24 shown in FIG. 2 as described herein.

The drive rod or spindle 5 can be supported at the bearing points 30. Between the end provided with the engaging element 5a and the spiral-toothed end section 5b, the drive rod or spindle 5 can include a cylindrical axis and in this area has an entrained braking device 31 for generating a minimal braking torque (in the range of 0.5 to 1.0 Nm), which can also generate an axial advance when idling, for example, in the non-engaged state of the discharging rod with the corresponding discharge plunger. The braking element 31 can also serve as a position marker for labeling the axial position of the discharging rod in the field of view of an operator or for an optical detection device or can bear such a marking element. In accordance with an exemplary embodiment, the second discharging rod (like the first discharging rod) can move forward, and thus whether correct discharging of component B is taking place. Thus, failure caused, for example by lack of correct engagement between the discharging rod and the separate discharge plunger, can be recognized immediately and the occurrence of incorrect adhesion points can be suppressed.

FIG. 6 shows a sectional view of additional essential parts of the transmission unit 8 with the discharging rods 4 and 5 in place to make their position assignment clear. With regard to the screw drive 25' for driving the first discharging rod 4, the construction can be modified versus the transmission component 25 sketched in FIG. 2 as well as FIGS. 3A and 3B.

FIGS. 7A and 7B show further detail of the braking element 31 illustrated in FIG. 5, which can be an entrained wrap spring housing, and the wrap spring 31a is also visible. FIG. 7B shows an exemplary embodiment of the braking element as an entrained plastic brake 31'. Both brake element designs are known to those skilled in the art and therefore will not be explained further.

FIG. 8 shows schematically on a block diagram the structure of a sensor system and the associated control means of the proposed drive device. The sensor system, in addition to the previously-mentioned microswitch 12, can include on the on/off switch ("trigger") 13a, serving as the primary operating element, or in addition to this or as a sensory replacement for it, and a current detection unit 32 for detecting the machine current of the drive machine 9, which can be supplied to this over a machine control 33. The drive control unit 14 can include a sensor signal processing unit 14a, a delay element 14b and a control signal outlet unit 14c.

A processing algorithm can be implemented in the sensor signal processing unit 14a, the signals from the microswitch 12, which can contain information on the discharge of component A, can be placed in an appropriate relationship to data originating from the on/off switch 13a or the current detection unit 32 and can provide information on the operating state of the machine. The processing result can also be subjected to an appropriate chronological evaluation (likewise based on stored algorithms) in the delay element 14b, and as a result, a suitable machine control signal can be emitted in all operating situations of the application device by the control signal output unit 14c.

Figure 9A:
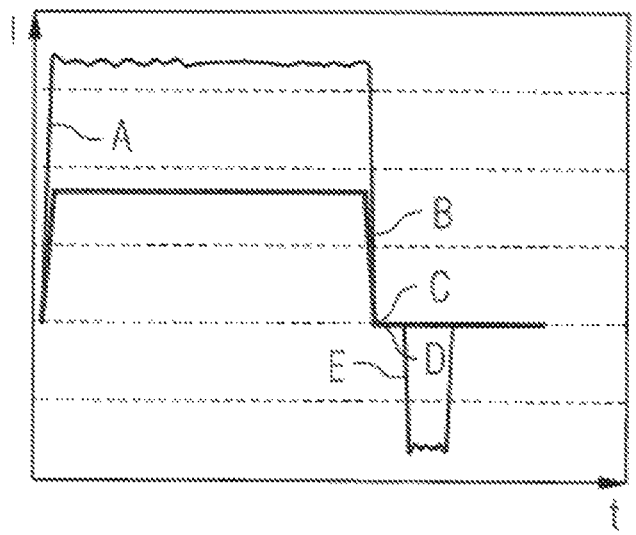
FIGS. 9A and 9B are exemplary machine current-time diagrams for exemplary embodiments of a control sequence of the drive control.
Figure 9B:
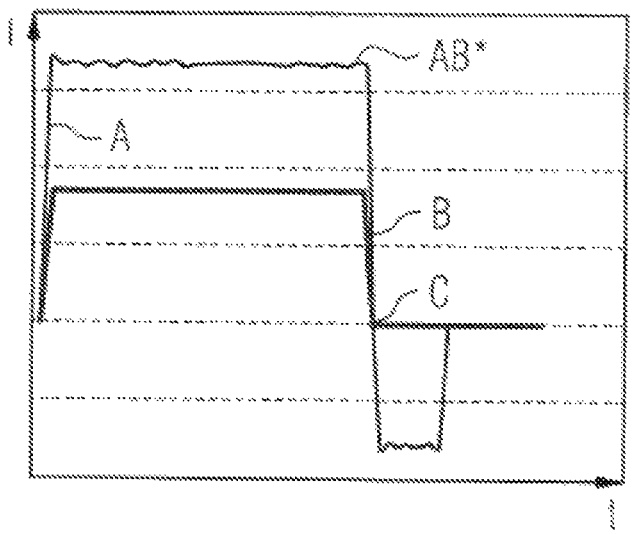

FIGS. 9A and 9B show time sequences based on machine current-time diagrams, which each start at a point A with an increase in the detected machine current I based on a turning-on action of the on/off switch 13a. At point B in FIG. 9A an on/off switch is slowly released; at point C the flow detection unit 32 detects a machine current value of 0, after which, during a brief phase D, the sensor signal processing unit 14a tests whether the machine current remains at the value of 0 to determine whether the on/off switch was released deliberately or accidentally. If the former is the case, then at point E the signal from the still-depressed microswitch 12 can be processed, such that control signal output unit 14c ultimately emits a signal that causes a return stroke of the machine 9.

FIG. 9B shows an alternative version of a comparable control sequence. Here in the sensor signal processing unit 14a before time B (release of the on/off switch) in a phase AB* the machine current value is detected and stored and used for comparison with the current value measured at time point C. Here the processing unit recognizes, based on the comparison result, whether the on/off switch was deliberately released, and as long as a corresponding signal is available from the microswitch 12, starts the machine return stroke at practically the same time.

With the procedure described in both variants, an unnecessary return stroke of the machine in case of accidental or very brief release of the trigger can be prevented, but at the same time a return stroke that is appropriate because of deliberate termination of the drive process can be initiated, so that an "overshooting" discharge of multi-component materials, especially component A (which would still be under drive pressure if the machine were simply turned off) can be suppressed. At the same time, with the (slight) return stroke and with the end of effect of the reaction force coming from component A the second transmission component group 19 can be made to return to its initial position at a maximum distance from the first component group 18, thus releasing the coupling 24 and the microswitch 12. This can be a suitable shutoff and non-use state of the application device.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. A drive apparatus of a metering and mixing device for multi-component materials, the drive apparatus comprising:
    at least two cartridge-accommodating devices configured to accommodate replaceable cartridges with individual material components, respectively, wherein a first one of the at least two cartridge-accommodating devices is configured to accommodate a first one of the replaceable cartridges containing a first one of the material components, and a second one of the at least two cartridge-accommodating devices is configured to accommodate a second one of the replaceable cartridges containing a second one of the material components configured to react with the first one of the material components when the first and second material components are respectively discharged from the first and second cartridges;

a discharging device configured to simultaneously discharge the material components from the cartridges through component outlets with the aid of first and second discharging plungers for respectively plunging into a corresponding one of the first and second cartridge-accommodating devices or the first and second cartridges;

a mixing device connected to the component outlets for mixing discharged material components and discharging the material components in mixed form; and a transmission unit for connection to a drive machine, wherein the transmission unit includes a coupling for a forced connection of the discharge of the first and second material components by correspondingly synchronized actuation of the first and second discharging plungers via a corresponding one of a first discharging rod and a second discharging rod, so that the first one of the material components is discharged only if the second one of the material components is discharged simultaneously.

2. The drive apparatus according to claim 1, comprising:
an axial drive of the first discharging plunger driven over the first discharging rod for discharging the first one of the material components and for rotary drive of the second discharging plunger driven over the second discharging rod for discharging the second one of the material components, wherein the second discharge plunger is threaded, and wherein the second discharging rod is spindle-like.

3. The drive apparatus according to claim 2, comprising:
a component group that is movable axially under reactive pressure during the discharge of the first one of the material components.

4. The drive apparatus according to claim 3, comprising:
a switchable coupling device, which is configured to connect the second discharging rod to the drive machine of the transmission unit when the movable component group has moved by a predetermined amount under the reaction pressure.

5. The drive apparatus according to claim 4, wherein the switchable coupling device comprises:
a first coupling element, which is fixed in an axial direction with respect to the drive machine; and
a second coupling element which is fixed in the axial direction with respect to the movable component group, such that the second coupling element will move with the component group under the reactive pressure and, during its displacement, come to engage with the first coupling element.

6. The drive apparatus according to claim 4, wherein the switchable coupling device is a form-locking coupling.

7. The drive apparatus according to claim 4, wherein the switchable coupling device is a claw coupling.

8. The drive apparatus according to claim 6, comprising:
die coupling elements of the form-locking coupling, which are self-locating elements.

9. The drive apparatus according to claim 4, wherein the switchable coupling device is a force-locking coupling.

10. The drive apparatus according to claim 4, wherein the switchable coupling device is a frictional coupling.

11. The drive apparatus according to claim 2, comprising:
a counter-pressure spring element for supplying a counter-pressure force directed against the reactive pressure built up during discharge of the first one of the material components.

12. The drive apparatus according to claim 11, comprising:
a forward pressure spring element for supplying an adjusting pressure force directed parallel to the counter-pressure during discharging of the first one of the material components.

13. The drive apparatus according to claim 12, wherein at least one of the counter-pressure spring element and the forward pressure spring element is a coil spring, plate spring or leaf spring made of metal.

14. The drive apparatus according to claim 2, wherein the first discharging rod is a gear rack, and the transmission unit includes at least one drive gear.

15. The drive apparatus according to claim 14, wherein the at least one drive gear of the transmission unit associated with the gear rack of the first discharging rod is movably mounted with regard to the gear rack for mechanical decoupling from the gear rack.

16. The drive apparatus according to claim 2, wherein the second discharging rod possesses a rear end part and a front part relative to a position in use, wherein at the rear part the second discharging rod has a spiral-toothed, non-self-locking spindle section,
wherein at the front part the second discharging rod has an engaging element for engaging in the second discharging plunger, and
wherein the transmission unit has a driven gear spiral-toothed in its interior, adapted to the spiral-toothing of the spindle section.

17. The drive apparatus according to claim 16, comprising:
an entrained braking element in a front section of the second discharging rod and outside of the spiral-toothed spindle section, wherein the braking element is configured to provide axial movement of the discharging rod during idling.

18. The drive apparatus according to claim 1, comprising:
a rotary shaft connection for connecting a drive shaft of the transmission unit to an active mixer in the metering and mixing device.

19. A device for multi-component materials, the device comprising:
an integrated electric drive machine;
an operating and control unit;
a battery power supply for the integrated electric drive machine and the operating and control unit; and
a drive apparatus of a metering and mixing device, the drive apparatus including:
at least two cartridge-accommodating devices configured to accommodate replaceable cartridges with individual material components, respectively, wherein a first one of the at least two cartridge-accommodating devices is configured to accommodate a first one of the replaceable cartridges containing a first one of the material components, and a second one of the at least two cartridge-accommodating devices is configured to accommodate a second one of the replaceable cartridges containing a second one of the material components configured to react with the first one of the material components when the first and second material components are respectively discharged from the first and second cartridges;
a discharging device configured to simultaneously discharge the material components from the cartridges through component outlets with the aid of first and second discharging plungers for respectively plunging into a corresponding one of the first and second cartridge-accommodating devices or the first and second cartridges;

a mixing device connected to the component outlets for mixing the discharged material components and discharging the material components in mixed form; and a transmission unit for connection to a drive machine, wherein the transmission unit includes a coupling for a forced connection of the discharge of the first and second material components by correspondingly synchronized actuation of the first and second discharging plungers via a corresponding one of a first discharging rod and a second discharging rod, so that the first one of the components is discharged only if the second one of the components is discharged simultaneously.

* * * * *